United States Patent [19]

McDonald et al.

[11] Patent Number: 5,348,670
[45] Date of Patent: Sep. 20, 1994

[54] PHOSPHOROUS AMINE LUBRICANT ADDITIVES

[75] Inventors: Randolph A. McDonald, Berea; Gerald D. Burt, Moreland Hills, both of Ohio

[73] Assignee: The Elco Corporation, Cleveland, Ohio

[21] Appl. No.: 13,510

[22] Filed: Feb. 4, 1993

Related U.S. Application Data

[60] Continuation-in-part of Ser. No. 911,839, Jul. 10, 1992, Pat. No. 5,194,166, which is a division of Ser. No. 526,080, May 18, 1990, Pat. No. 5,130,036.

[51] Int. Cl.$^5$ .................. C10M 137/02; C07F 9/02
[52] U.S. Cl. .................. 252/32.5; 252/49.9; 252/49.8; 252/50; 252/51; 252/51.5 A; 558/81; 558/108; 558/170
[58] Field of Search .................. 252/49.9, 49.8, 32.5, 252/50, 51, 51.5 A; 558/81, 108, 170

[56] References Cited

U.S. PATENT DOCUMENTS

| | | | |
|---|---|---|---|
| 2,018,758 | 10/1935 | Ellis | 252/51.5 A |
| 3,553,131 | 1/1971 | Hepplewhite et al. | 252/46.7 |
| 4,293,432 | 10/1981 | Papay et al. | 252/49.9 |
| 4,400,284 | 8/1983 | Jessup et al. | 252/49.6 |
| 4,427,560 | 1/1984 | Holstedt et al. | 252/42.7 |
| 4,490,265 | 12/1984 | Holstedt et al. | 252/47.5 |
| 4,522,629 | 6/1985 | Horodysky et al. | 44/315 |
| 4,529,528 | 7/1985 | Horodysky | 252/49.6 |
| 4,532,057 | 7/1985 | Horodysky et al. | 252/49.8 |
| 4,533,480 | 8/1985 | Holstedt et al. | 252/46.4 |
| 4,555,353 | 11/1985 | Horodysky et al. | 252/49.6 |
| 4,557,843 | 12/1985 | Holstedt et al. | 252/46.4 |
| 4,557,844 | 12/1985 | Horodysky | 252/49.9 |
| 4,557,845 | 10/1985 | Horodysky et al. | 252/49.9 |
| 4,587,026 | 5/1986 | Horodysky | 252/47.5 |
| 4,778,610 | 10/1988 | Horodysky | 252/32.5 |
| 4,857,214 | 8/1989 | Papay et al. | 252/32.5 |
| 4,965,002 | 10/1990 | Brannen et al. | 252/49.9 |
| 5,130,036 | 7/1992 | Burt et al. | 252/32.5 |
| 5,194,166 | 3/1993 | Burt et al. | 252/32.5 |

FOREIGN PATENT DOCUMENTS

| | | |
|---|---|---|
| 152677 | 8/1985 | European Pat. Off. |
| 302334 | 2/1989 | European Pat. Off. |
| 115792 | 9/1981 | Japan |
| 423797 | 4/1974 | U.S.S.R. |
| 451702 | 11/1974 | U.S.S.R. |

Primary Examiner—Prince Willis, Jr.
Assistant Examiner—Alan D. Diamond
Attorney, Agent, or Firm—Panitch Schwarze Jacobs & Nadel

[57] ABSTRACT

Lubricant additives are disclosed which are produced by reacting an alkanolamine, a carboxylic acid and phosphorous acid. The reaction product may also include a boron compound and/or a monofunctional alcohol. The additives are useful in combination with metalworking oils, particularly in extreme pressure applications, to replace currently used chlorinated paraffin additives.

14 Claims, No Drawings

PHOSPHOROUS AMINE LUBRICANT ADDITIVES

CROSS-REFERENCE TO RELATED APPLICATIONS

The present application is a continuation-in-part of copending U.S. Patent application Ser. No. 07/911,839, filed Jul. 10, 1992, now U.S. Pat. No. 5,194,166, which is a division of U.S. Patent application Ser. No. 07/526,080, filed May 18, 1990, entitled "Phosphorous Amine Lubricant Additives", now U.S. Pat. No. 5,130,036.

FIELD OF THE INVENTION

The present invention relates to reaction products which are useful as lubricant additives. More particularly, the invention is directed to lubricant additives which can replace conventional chlorinated paraffins in applications such as extreme pressure metalworking.

BACKGROUND OF THE INVENTION

Chlorinated paraffin waxes, particularly higher molecular weight solid or liquid chlorinated paraffins in the $C_{10}$ to $C_{30}$ range, have been widely used for over fifty years in metalworking, for example, as lubricant additives in drawing oils, extrusion oils and soluble oils, and particularly for extreme pressure applications. Chlorinated waxes are used almost exclusively in drawing oils, and chiefly in mineral oils. In extrusion oils, the additives usually include phosphorous and sulfur compounds due to the severity of operations. In soluble oils the chlorinated waxes are usually used in combination with fats or lard oils.

In 1977, twenty percent (40,000 tons) of the free-world production of liquid chlorinated paraffins was used in oil applications. However, in recent years, concern has arisen regarding toxicity and possible carcinogenicity of chlorinated paraffins. With the banning of chlorinated waxes in Germany and Canada, and the requirement of placing warning labels on drums of these materials in this country, alternative lubricant additives are being sought.

While many in the metalworking industry have switched to chlorinated olefins and polyesters to replace chlorinated paraffins, there is a concern among some that these chlorinated products may also have carcinogenic properties. Therefore, non-chlorinated substitutes are considered desirable. While sulfonated products have been considered satisfactory for light machining applications, they have not been generally satisfactory for heavier machining, such as the severe metal cuts and draws for which use of the chlorinated paraffins has been favored.

In the past, a number of non-chlorine containing additives have been developed to provide lubricating oil compositions with enhanced friction characteristics for use in engine and machinery lubricating oils and fuels. Such additives have included phosphorous compounds such metal phosphonates, alkali metal salts of alkylphosphonic acids, and dihydrocarbyl hydrocarbylphosphonates; amines, such as alkoxylated amines; and certain boron-containing compounds. Examples of these prior art lubricating oil additives are discussed, for example, at column 1 of U.S. Pat. No. 4,529,528.

Published European Patent Application No. 152,677 discloses borated alkoxylated amines as thickeners for water-based functional fluids. Borated alkoxylated amines are also disclosed in U.S. Pat. Nos. 4,400,284; 4,427,560; 4,490,265; 4,533,480 and 4,557,843 of Union Oil Company as intermediates for extreme pressure, anti-wear additives in lubricating compositions.

A series of additives has also been developed by Mobil Oil Corporation which are reaction products (essentially mixtures of simple and complex esters) of organic amines and organic phosphonates or phosphites. Early examples of such compositions are disclosed in U.S. Pat. No. 3,553,131 of Hepplewhite et al., in which $C_6$–$C_{40}$ diaryl phosphonates (phosphites) are reacted with primary, secondary, or tertiary organic amines to produce products or mixtures which are incorporated in ester lubricants which are alleged to have higher load-carrying properties, surprising stability under storage and are relatively non-corrosive to metals.

A more recent series of patents to Horodysky et al., assigned to Mobil, discloses engine lubricant and fuel additives which are the reaction product of a phosphorous compound, particularly a $C_1$–$C_6$ dihydrocarbyl phosphite, with an alkoxylated amine or a vicinal diol, with or without a boron compound, such as boric oxide, a metaborate, boric acid, or an alkyl borate. See, for example U.S. Pat. Nos. 4,529,528; 4,557,845; 4,557,844; 4,555,353; 4,532,057 and 4,522,629. Mobil U.S. Patent No. 4,587,026 also discloses borated N,N-bis(2-hydroxpropyl)cocamine in the presence of dodecyl phenol sulfide as a friction-reducing, high temperature stabilizing additive.

While the reaction products of Hepplewhite and Horodysky, et al. are disclosed as possible additives for use with engine lubricating oils or greases, and as additives to liquid fuels such as gasoline, fuel oil and diesel oil, there is no disclosure of using these compounds for the severe requirements of metalworking fluid additives. Moreover, tests by the present inventors of several of the Horodysky et al. products have shown serious disadvantages in using such products as additives for metalworking fluids, particularly in extreme pressure (EP) applications.

U.S. Pat. No. 4,857,214 also discloses phosphorous-containing compounds useful as additives in lubricants. The compounds disclosed comprise the oil soluble reaction product of an inorganic phosphorous acid or anhydride, a boron compound and an ashless dispersant. The preferred acid is phosphorous acid. The ashless dispersant may be, e.g., a hydrocarbyl succinimide, a mixed ester/amide of hydrocarbyl-substituted succinic acid, hydroxyesters of hydrocarbyl-substituted succinic acid, and the Mannich condensation products of hydrocarbyl-substituted phenols, formaldehyde and polyamines. Additional sources of nitrogen such as N-tallow diethanolamine may also be used in combination with the ashless dispersant. However, there is no disclosure of using the reaction product of an alkanolamine, carboxylic acid and phosphorous acid as a metalworking lubricant additive.

U.S. Pat. No. 4,965,002 discloses lubricant additives useful for metalworking and extreme pressure applications produced by reacting an alkoxylated amine with a disubstituted organic phosphite. The additives preferably also contain a boron moiety which is reacted with the phosphite and the amine.

U.S. Pat. No. 5,130,036 discloses phosphorous amine lubricant additives for metalworking and extreme pressure applications produced by reacting an alkoxylated amine with phosphorous acid. The additives may also include a boron moiety, a mono-functional alcohol and/or a long-chain aliphatic carboxylic acid.

BRIEF SUMMARY OF THE INVENTION

According to the present invention, a lubricant additive is provided which is the reaction product of an alkanolamine of the formula (I):

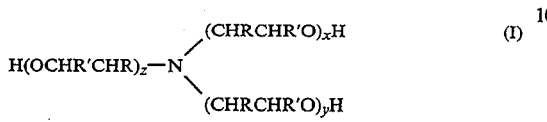

wherein each of R and R' is independently selected from the group consisting of hydrogen and a $C_1$ to $C_6$ alkyl group and x, y and z are each integers of from 0 to 10, at least one of which is not 0, and preferably at least two of these are not 0, with an aliphatic carboxylic acid of the formula (II):

wherein $R^3$ is a $C_1$ to $C_{30}$ hydrocarbon group and phosphorous acid. The reaction is carried out at a temperature of about 50° to about 250° C. and the molar ratio of the alkanolamine to the phosphorous acid is about 0.1:1 to 10:1.

The reaction product may also include a compound selected from the group consisting of: (1) a boron compound selected from boric oxide, a metaborate or a compound of the formula (III):

wherein $R^4$ is a $C_1$ to $C_6$ alkyl group, and m and n are 0 to 3, their sum being 3; and (2) an alcohol of the formula (IV):

wherein $R^5$ is a $C_1$ to $C_{30}$ hydrocarbon group.

The present invention also includes lubricating oil compositions, particularly metalworking oils, containing the above-discussed reaction products as additives. These lubricating compositions may include as the major component mineral oils or synthetic oils, including so-called "soluble oils", for use in forming aqueous emulsion lubricants. The invention also includes the use of the lubricant additives in metalworking operations, particularly extreme pressure operations.

DETAILED DESCRIPTION OF THE PREFERRED EMBODIMENTS

The compounds or complexes of the present invention are produced by reacting (a) an alkanolamine of formula (I) with (b) a carboxylic acid of formula (II) and (c) phosphorous acid ($H_3PO_3$) to produce a lubricant additive.

Although applicants do not wish to be bound by any theory, it is believed that the simplified reaction of (a) the alkanolamine of formula (I) when z is 0 and x and y are each 1, and (b) carboxylic acid generally proceeds as follows:

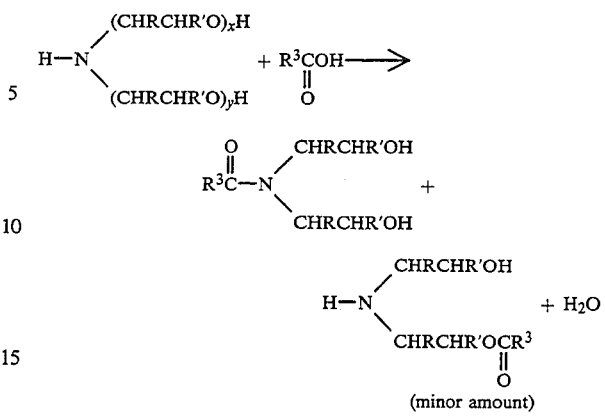

The product of the reaction between the alkanolamine and carboxylic acid reacts with (c) the phosphorous acid to form the product, as represented by the following non-limiting reaction equation:

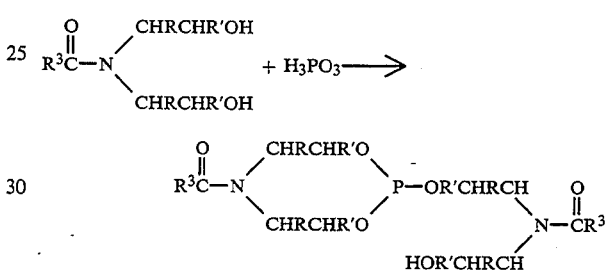

In other words, the aliphatic carboxylic acid esterifies at least one of the —OH groups on the alkanolamine. The phosphorous acid may then react with the product of the reaction between the alkanolamine and carboxylic acid to form the final product. Additional alkanolamine may be added to the final product mixture to react with substantially all of the phosphorous acid. It will be evident to one skilled in the art that other similar products may be formed by this reaction and that other mechanisms or reaction routes may occur. It is believed that the order of addition of the reactants is not particularly critical and that the reactants could be reacted simultaneously or pairs of reactants pre-reacted, as desired.

The compounds or complexes of the present invention are referred to as reaction products since the exact structures of these compounds are not known. While applicants do not wish to be bound by any particular theory, it is believed that the reaction products are mixtures of a number of different simple and complex esters, including possibly cross-linked species and/or prepolymers.

The reactions of the alkanolamine, carboxylic acid and phosphorous acid to form the product are conducted at temperatures ranging from about 50° C. to about 250° C., and preferably about 120° C. to about 180° C. One of ordinary skill in the art would understand, however, that the temperatures at which the reaction is conducted may vary based upon the use of different compounds in the reaction, different pressures at which the reaction may be conducted, etc. It is preferred that the reaction be conducted at atmospheric pressure (1 atm).

The reaction of the various components described above proceeds readily under low to moderate heat, such as about 80° C. to 200° C., and preferably about 150° C. to 160° C. The optimum reaction time varies with the amount of boron being used, if any, but in general the reaction time should not exceed about 2.5 to 3 hours. During heating, the water formed as a by-product may be removed by azeotropic distillation, and the cessation of the evolution of water generally marks the end of the reaction. For products containing higher amounts of boron, the reaction time may be about 3 hours. In the absence of boron or for low amounts of boron, 1.5 hours should be a sufficient reaction time. Moreover, the present reaction is preferably carried out in the presence of a nitrogen blanket.

Preferably, the ratio of alkanolamine to carboxylic acid is about 0.5:1 to about 2:1, and more preferably about 1:1. Molar ratios of alkanolamine to phosphorous acid in the range of about 0.1:1 to about 10:1 are believed to be satisfactory for use in the present invention. It is preferred that the molar ratio of alkanolamine to phosphorous acid be about 0.5:1 to about 2:1.

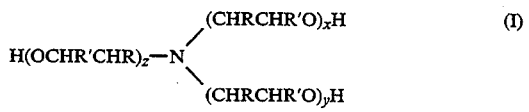
(I)

wherein each of R and R' is selected from the group consisting of hydrogen and a $C_1$ to $C_6$ alkyl group and x, y and z are each integers of from 0 to 10, at lease one of which is not 0, may be used in the present invention.

Examples of such alkanolamines include monoethanolamine, diethanolamine, triethanolamine, or isopropanolamine. Preferred alkanolamines for use in the present invention include monoethanolamine, diethanolamine and isopropanolamine.

Aliphatic carboxylic acids of the formula (II):

(II)

wherein $R^3$ is a $C_1$ to $C_{30}$ hydrocarbon group, and preferably a $C_{14}$ to $C_{30}$ hydrocarbon group, may be used in the present invention. The carboxylic acids preferred for use in the present invention include long-chain aliphatic carboxylic acids, such as oleic acid, stearic acid, myristic acid, palmitic acid, palmitoleic acid, linoleic acid and dimer acids having more than 14 carbon atoms. Suitable carboxylic acids include, for example, Acintol FA-2 tall oil fatty acid, which is commercially available from Arizona Chemical Company of Panama City, Fla. or Sylfat 96 of Sealand Chemicals of Cleveland, Ohio.

A boron compound of formula (III), or one or more of the other boron compounds identified above, may be included in the reaction of the alkanolamine, carboxylic acid and phosphorous acid. The boron compound may be included in an initial reaction of two of the three main components or in an essentially simultaneous reaction of all three reactant components, for example.

The boron compound is preferably selected from boric acid, a metaborate or a compound of the formula (III):

(III)

wherein $R^4$ is a $C_1$ to $C_6$ alkyl group, and m and n are 0 to 3, their sum being 3. The reaction including the boron compound is conducted at a temperature similar to that of the reaction of the alkanolamine, carboxylic acid and phosphorous acid. The optimum reaction time varies with the amount of boron used, as discussed above.

Where a boron compound is present in the reaction mixture, the molar ratio of alkanolamine to boron compound is in the range of about 30:1 to about 1:1. The ratio of phosphorous acid to boron compound is generally about 0.5:1 to about 20:1, and preferably about 1:1 to about 15:1. Generally a solvent is not needed to facilitate the reaction in the absence of boron or in the presence of low amounts of boron. However, the use of higher amounts of boron compound provides generally superior results in various metalworking tests and operations.

In addition to boric acid and metaborates, the boron compounds useful in the present invention include boric acid; mono-, di- and trimethyl borates; mono-, di- and tripropyl borates; mono-, di- and tributyl borates; mono-, di- and triamyl borates; mono-, di- and trihexyl borates; and silica borates. Boric acid is preferred since it is readily available and generally low in cost.

The products of the present invention, with or without the additional boron compound, are highly effective in Falex EP tests in both oil and aqueous systems. However, some of these reaction products are somewhat viscous and have somewhat less solubility than desired due to cross-linking, i.e., polymerization, in the product. Accordingly, it is preferred to modify the reaction in order to lower the viscosity and increase the solubility of the reaction product.

Therefore, a monofunctional alcohol may be added to the reaction to decrease the extent of polymerization in the final product. Monofunctional alcohols useful in the present invention are represented by formula (IV), as follows:

(IV)

wherein $R^5$ is a $C_1$ to $C_{30}$ hydrocarbon group of 1 to 30 carbons. Preferred monofunctional alcohols are $C_{18}$ to $C_{26}$ alkyl alcohols.

Monofunctional alcohols useful in the present invention include synthetic alcohols of $C_{18}$ and $C_{26}$ chain length, such as Exxal 18 and Exxal 26, which are commercially available from Exxon Chemicals.

Although applicants do not wish to be bound by any particular theory, it is believed that a reaction of the product of the alkanolamine of formula (I) (where z is 0), carboxylic acid, phosphorous acid, and the monofunctional alcohol may be represented generally as follows:

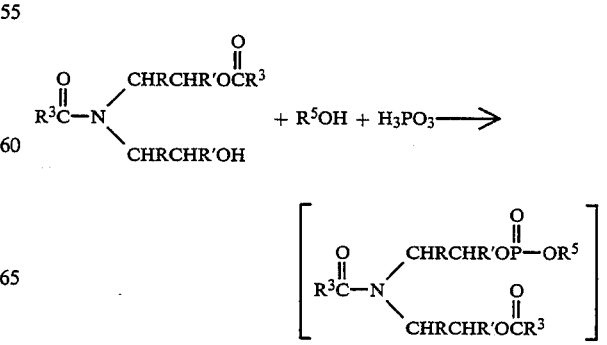

Again, it will evident to one of ordinary skill in the art that other products may be formed in this reaction and that other mechanisms or reaction routes may occur.

The reaction may be carried out in the presence of a solvent, preferably a liquid hydrocarbon solvent such as toluene or xylene. Upon completion of the reaction the solvent and any by-product alcohol may be removed, e.g., by vacuum stripping. However, reactions in which there is a low amount of boron compound generally need no solvent, due to the small amount of water evolved by the esterification reaction. If desired, a nitrogen blanket may be used to help decrease darkening of the product by oxidation.

The reaction may also be carried out in the presence of a catalyst to encourage amide formation over ester formation. Suitable catalysts include, for example, boron trifluoride, sodium hydroxide and similar bases. One of ordinary skill in the art would understand that different catalysts may be used in different amounts, in keeping with the spirit and scope of the present invention.

Products of the present invention in the acid pH range (below 7) are generally more effective in metalworking applications. However, the product should not be too acidic since the metal upon which the product may be applied may corrode. Generally, the compounds of the present invention are good rust inhibitors and do not require adjustment of acidity.

If a compound of the present invention has a pH of less than about 5.5, it is desirable to adjust or pacify the pH to about 5.5 to about 7, and preferably about 6 to about 6.5, with an oil soluble amine. Suitable amines for adjusting the pH of products of the present invention include mixtures of long-chain primary amines, such as PRIMENE 81R, which is commercially available from Rohm & Haas Co. of Philadelphia, Pa., or dimethyl decyl amine, such as the product ADMA $C_{10}$, which is commercially available from Ethyl Corporation. Other pacifiers include commercially available rust inhibitors which are well known to those of ordinary skill in the art.

The compounds of the present invention are particularly useful as additives in various metalworking fluids to increase the lubricating capacity of the lubricating fluid and to reduce friction between metal parts. However, it will be understood by those skilled in the art that the compounds of the present invention may also be used in other lubricating environments in capacities such as engine additives and machinery lubricating oils.

The compounds of the present invention appear to be useful for the full range of metalworking fluids from mineral oils to synthetic oils to so-called soluble oils, the latter being emulsifiable in water for more preferred aqueous metalworking environments which provide greater cooling capacity to the metalworking operation. Thus, the additives of the present invention are readily soluble in and compatible with any of the aforementioned metalworking fluids. Further, the compounds of the present invention may be used in conjunction with other metalworking fluid additives or formulation components, such as sulfurized esters and active and passive sources of sulfur. Other additives, including corrosion inhibitors, surface active agents, thickeners for forming greases, and additives for specialized formulation uses, may also be included.

In general, the compounds of the present invention are soluble in paraffinic or naphthenic base stocks up to at least about 10 weight percent, which is the practical limit for use. When used in mineral oils or other synthetic lubricating oils, the compounds of the present invention are generally added in concentrations of about 0.1 to 10 weight percent and typically about 1 to 6 weight percent. When used as additives to soluble oils which will be emulsified in aqueous metalworking formulations, the compounds of the present invention are added in concentrations of about 0.1 to about 20 weight percent and preferably about 0.25 to about 10 weight percent.

The compounds of the present invention, when added to metalworking fluids, provide a high degree of lubricity in any of a wide variety of metalworking or machining operations, including broaching, threading, tapping, reaming, gear cutting, deep drilling, milling, boring and various automatic screw machine operations. However, the compounds of the present invention are particularly advantageous in extreme pressure (EP) operations. When used to replace chlorinated paraffins or combinations of chlorinated paraffin with lard oil, the compounds of the present invention have been found to perform similarly to or better than such conventional additives in a variety of lubricants, including drawing oils, tapping oils, gear oils and water-based metalworking formulations. For example, the use of long-chain aliphatic carboxylic acids of formula (II) in combination with alkanolamines and phosphorous acid (and preferably, boric acid) of the present invention, results in a product having a similar or superior Falex fail loads and increased 4-Ball EP LWIs (Load Wear Indices) when compared to typical prior art lubricant additives.

The invention will now be illustrated in more detail by reference to the following specific, non-limiting examples:

EXAMPLE A

The following components were added to a 1 liter three-neck round bottom flask fitted with a stirrer, condenser and Dean-Stark trap:

TABLE I

| Component | Grams | Moles |
| --- | --- | --- |
| Acintol FA-2 tall oil fatty acid | 322.9 | 0.986 |
| diethanolamine | 93.1 | 0.89 |
| boron trifluoride | 0.1 | 0.0015 |

Boron trifluoride was used as a catalyst to encourage amide formation rather than ester formation. The mixture was stirred and heated at a temperature of about 150°–160° C. for about 3 hours until substantially all of the water was evolved and removed (about 24 ml) to form an intermediate reaction product. To 109.5 g (0.33 moles) of this intermediate product was added an additional 50.4 g of Acintol FA-2 tall oil fatty acid and the mixture was heated to a temperature of about 140° C., at which time 13.9 g (0.17 moles) of phosphorous acid ($H_3PO_3$) was added thereto. The resulting mixture was heated at a temperature of about 145°–165° C. for about 1 hour under a nitrogen blanket. The resulting product was a viscous dark yellow liquid.

EXAMPLE B

The following components were added to a three-neck round bottom flask similar to that of Example A:

TABLE II

| Component | Grams | Moles |
| --- | --- | --- |
| Acintol FA-2 tall oil fatty acid | 531.9 | 1.74 |
| isopropanolamine | 118.7 | 1.58 |
| NaOH | 1.29 | 0.03 |

Sodium hydroxide was used as a catalyst to encourage amide rather than ester formation. The mixture was stirred and heated at a temperature of about 150° under a nitrogen blanket until about 30 ml of water was removed. A portion of the resulting intermediate product (216.9 g) was heated to about 135° C. under a nitrogen blanket. Next, 18.9 g of phosphorous acid was added to the mixture and the resulting reaction product was heated at 135° C. for 1 hour. The reaction product was cooled to room temperature (about 25° C.) and filtered through a 3 micron paper filter available from Millacron Corporation using Fibercell F-7, a diametaceous earth filter aid, to yield a clear, amber-colored viscous liquid product.

Test Results

The products of Examples A and B were tested in several standard tests which have been developed to evaluate desirable characteristics of metalworking fluids, as described below. In these tests, the compounds of the present invention were compared to one or more of the following commercially available lubricants: (1) LUBRIZOL LZ-5347, a PEP metalworking additive containing carbonated alkylbenzene sulfonate and (2) a standard additive formulation comprising 25% P145 chlorinated wax (40% chlorine), which is commercially available from Dover Chemical Corp., and 75% lard oil. The test results are set forth in Table III below.

TABLE III

| Additive | Falex EP *Fail Load (lbs) | 4-Ball EP Non-Seizure (lbs) | LWI | Weld Load (lbs) |
| --- | --- | --- | --- | --- |
| Example A | 4,700 | 100 | 44.3 | 250 |
| Example B | 4,450 | 80 | 34.3 | 200 |
| Lubrizol 5347 | x4,100 | 50 | 27.6 | 160 |
| Chloroparaffin-lard oil | 4,500+ | 80 | 32.9 | 250 |

*Values greater than 4,500 lbs are "off-scale" estimated values.
xExcessive smoke and blackening of the pin and V blocks occurred during testing.

Five weight percent of each additive was dissolved in Exxon 150N mineral oil. The 4-Ball EP test (ASTM D-2783) measures the extreme pressure characteristics of a lubricant as indicated by the load wear index (LWI) and the weld load. The 4-Ball EP test is conducted by rotating a test ball under load, the test ball being located at a tetrahedral position on top of three stationary balls which rest in the test lubricant. Measurements of scars on the three stationary balls are used to calculate the LWI value. The weld load is the load at which the four balls weld together after ten seconds. It is desirable to have high LWI values, high weld loads and high non-seizure loads. The values of non-seizure loads are also set forth in Table III. The non-seizure load values are determined according to ASTM Method D2783-82. Generally, the non-seizure load is the last load at which the measured scar diameter is not more than 5% above the compensation line at the load.

The Falex EP tests are conducted on a Falex (FAVILLE-LeVALLY) lubricant tester, which is described, for example, in *United States Steel Lubrication Engineers Manual* at pp. 136-37. In this test, a brass pin revolves at 290 rpm between two steel blocks immersed in the test oil. The pressure exerted between the blocks on the pin is increased until the brass pin fails, either by sudden sheering or wear occurring at a rate faster than the load can be increased. The maximum measurable failure load is 4500 p.s.i.

Based on the test results shown in Table III, the compounds of the present invention, when added to mineral oil lubricants, show excellent metalworking properties as well as good corrosion resistance. The Falex EP fail load values (namely, 4700 and 4450 pounds, respectively) exceed the Falex EP fail load value of Lubrizol 5347 (4100 pounds). The Falex EP fail load values of Examples A and B are similar to that obtained for the chloroparaffin-lard oil blend.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the invention as defined in the appended claims.

We claim:
1. A lubricant additive comprising the reaction product of:
(a) an alkanolamine of the formula:

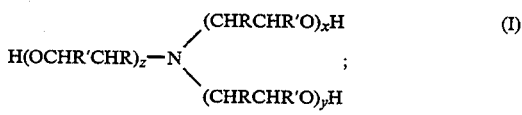
(I)

wherein each of R and R' are independently selected from the group consisting of hydrogen and a $C_1$ to $C_6$ alkyl group and x, y and z are each integers of from 0 to 10, at least one of which is not 0;
(b) an aliphatic carboxylic acid of the formula:

(II)

wherein $R^3$ is a $C_1$ to $C_{30}$ hydrocarbon group; and
(c) phosphorous acid;
wherein said reaction is carried out at a temperature of about 50° to about 250° C. and the molar ratio of said alkanolamine to said phosphorous acid is about 0.1:1 to about 10:1.

2. The product according to claim 1, wherein the molar ratio of said alkanolamine to said carboxylic acid is about 0.5:1 to about 2:1.

3. The product according to claim 1, wherein said alkanolamine is diethanolamine.

4. The product according to claim 1, wherein said alkanolamine is isopropanolamine.

5. The product according to claim 1, wherein the aliphatic carboxylic acid is a long-chain aliphatic carboxylic acid and $R^3$ is a $C_{14}$-$C_{30}$ hydrocarbon group.

6. The product according to claim 1, wherein the reaction is conducted at a temperature of about 150° to about 160° C.

7. The product according to claim 1, wherein (a) and (b) are reacted to form an intermediate and then said intermediate is reacted with (c) to form said reaction product.

8. The product according to claim 1, wherein the reaction of (a), (b) and (c) occurs essentially simultaneously.

9. A lubricant composition comprising a major proportion of a lubricating oil and a friction reducing amount of the product of claim 1.

10. A lubricant composition according to claim 9, wherein said lubricating oil is emulsifiable in water.

11. A lubricant composition according to claim 9, wherein the pH of said product is about 5.5 to about 7.

12. A composition according to claim 9, wherein said product is present in said oil in amount of about 0.1 to about 10 wt %.

13. A method of lubricating a metalworking operation comprising performing said operation in the presence of a lubricating oil containing the product of claim 1.

14. A method according to claim 13, wherein said operation is an extreme pressure operation.

* * * * *